United States Patent
Bell et al.

(10) Patent No.: US 7,145,014 B2
(45) Date of Patent: Dec. 5, 2006

(54) PROCESS FOR THE PREPARATION OF QUINOLINE DERIVATIVES

(75) Inventors: David Bell, Harlow (GB); Bryan John Davies, Harlow (GB); Peter Markham Kincey, Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 82 days.

(21) Appl. No.: 10/513,096

(22) PCT Filed: May 2, 2003

(86) PCT No.: PCT/EP03/04852

§ 371 (c)(1),
(2), (4) Date: Oct. 29, 2004

(87) PCT Pub. No.: WO03/093239

PCT Pub. Date: Nov. 13, 2003

(65) Prior Publication Data

US 2005/0165054 A1 Jul. 28, 2005

(30) Foreign Application Priority Data

May 3, 2002 (GB) .................................. 0210150.9

(51) Int. Cl.
*C07D 215/36* (2006.01)
*C07D 215/16* (2006.01)
(52) U.S. Cl. ...................................... 546/157; 546/153
(58) Field of Classification Search ................ 546/157, 546/153
See application file for complete search history.

(56) References Cited

FOREIGN PATENT DOCUMENTS

WO    WO 97/13753    4/1997
WO    WO 97/36590    10/1997

OTHER PUBLICATIONS

LaMontagne, J Med Chem, vol. 32, pp. 1728-1732, 1989.*

* cited by examiner

*Primary Examiner*—D. Margaret Seaman
(74) *Attorney, Agent, or Firm*—Kathryn L. Sieburth; Mary E. McCarthy; Charles M. Kinzig

(57) ABSTRACT

The invention relates to a process for the preparation of certain quinoline derivatives, in particular, 8-[(4-amino-1-methylbutyl)amino]-2,6-dimethoxy-4-methyl-5-(3-trifluoromethylphenoxy)quinoline succinate.

1 Claim, No Drawings

PROCESS FOR THE PREPARATION OF QUINOLINE DERIVATIVES

This application is a 371 of International Application No. PCT/EP03/04852, filed 02 May 2003.

The present invention relates to a process for the preparation of certain substituted quinoline derivatives, useful as antimalarial agents.

U.S. Pat. No. 4,617,394 discloses various quinoline compounds said to be useful as anti-malarial agents. One of these compounds, that is to say, 8-(4-amino-1-methylbutylamino)-2,6-dimethoxy-4-methyl-5-(3-trifluoromethylphenoxy) quinoline succinate (INN: tafenoquine) has been found to be particularly promising in clinical studies, and shows strong potential as an effective anti-malarial agent.

The quinoline structure of tafenoquine is complex, and the process for its preparation disclosed in U.S. Pat. No. 4,417,394 is an inefficient multi stage process which has a number of problems when applied to large scale manufacture of the compound.

An improved process for the manufacture of tafenoquine and related compounds has been disclosed in WO 97/13753 (published 17 Apr. 1997).

It has now been found that still further unexpected improvements can be made to the process disclosed in WO 97/13753 through the use of an alternative source of the 8-portion amino group which provides an improved synthesis of the protected intermediate precursor to the tafenoquine end product. This improvement in synthesis leads overall to a very efficient 8 stage synthesis of tafenoquine as compared to the 12 step process disclosed in U.S. Pat. No. 4,617,394.

Accordingly the present invention provides, in a first aspect:

a process for the preparation of a compound of structure (I) or a pharmaceutically acceptable salt thereof:

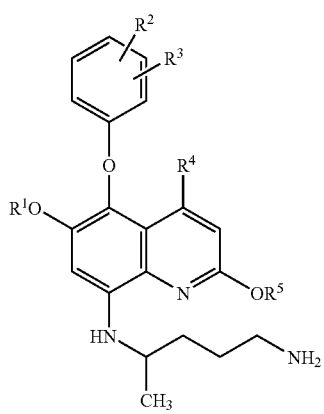

(I)

in which,
$R^1$ is $C_{1-6}$ alkyl,
$R^2$ and $R^3$ are independently hydrogen, halogen, trifluoromethyl, or $C_{1-6}$ alkoxy;
$R^4$ is $C_{1-6}$ alkyl; and
$R^5$ is hydrogen or $C_{1-6}$ alkyl which comprises, reacting a compound of structure (II)

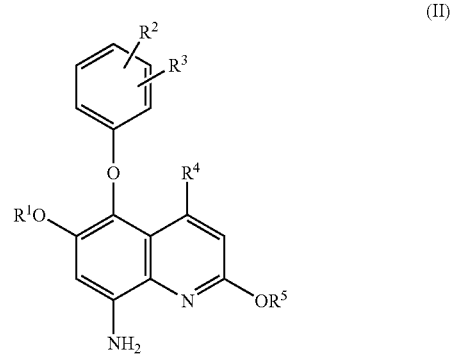

(II)

In which $R^1$ to $R^5$ are as described in structure (I) with a compound of structure (III)

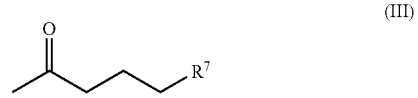

(III)

In which $R^7$ is $NH_2$, a protected amino group or a group convertable into an amino group to form a compound of formula (IV)

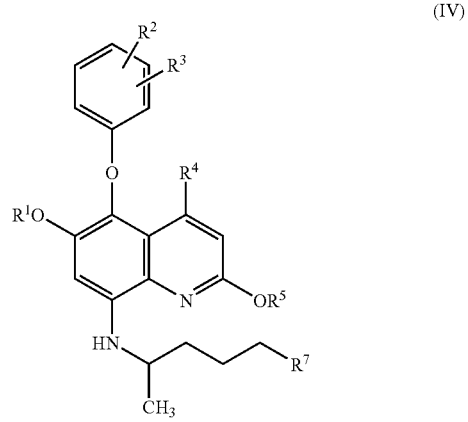

(IV)

in which $R^1$ to $R^5$ are as described in structure (I) and $R^7$ is amino or a protected amine group, and optionally thereafter,
 removing any protecting groups, and/or
 forming a salt.

Suitably, $R^7$ is $NH_2$, a protected amino group or a group convertable into an amino group. Preferably, $R^7$ is a protected amino group; most preferably a phthalimide group. Other forms of protected amino group will be apparent to the skilled person and include, for example, dibenzylamino. Suitable groups that can be readily converted into an amino group include, for example, nitro and cyano groups.

Suitably, the reaction between the compound of structure (II) and (III) is carried out under reductive alkylation conditions using a suitable reducing agent in a solvent or mixture of solvents. Preferably, the reaction is carried out using a borane-pyridine complex $BH_3$-pyridine) in acetic acid alone, or in a combination of acetic acid and tetrahydroftran or a $C_{1-4}$ alcohol such as methanol or ethanol as solvent. More preferably, the reaction is carried out using borane pyridine complex, in mixture of 20–30% acetic acid and 70–80% methanol as solvent, in particular, around 20% acetic acid and around 80% methanol. Most preferably, the reaction is carried out in acetic acid alone as a solvent.

In particular, the present invention can be used to prepare the compound tafenoquine, that is to say the compound of structure (IA)

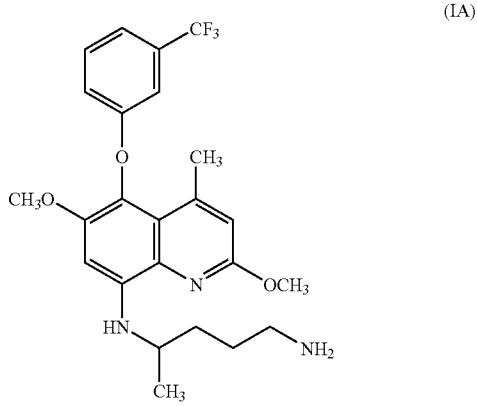
(IA)

by reaction of the appropriate precursor compound of structure (IIA), with the phthalimido derivative (IIIA)

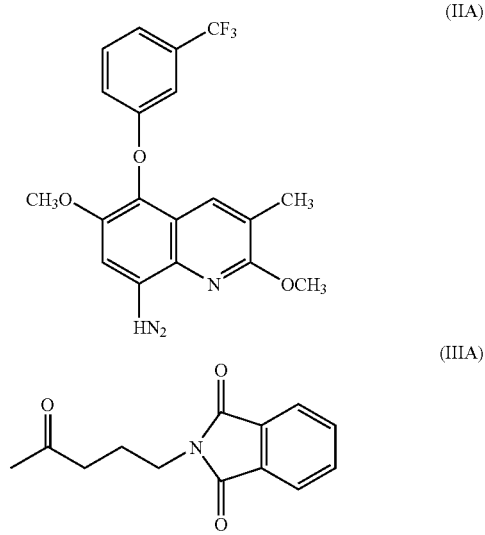
(IIA)

(IIIA)

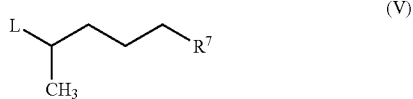

and thereafter, removing the phthalimide protecting group and forming the succinate salt.

It is to be noted that the preparation of compounds of structure (I) is achieved in the prior art (in WO 97/13753), by the reaction of the intermediate of structure (V),

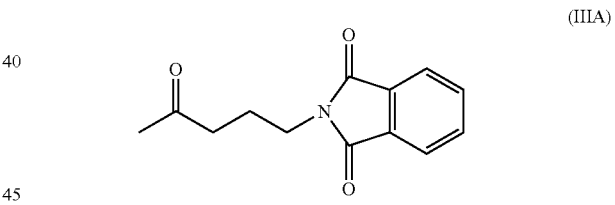
(V)

in which L is a leaving group, preferably halo, such as iodo and $R^7$ is amine or a protected amine group with compounds of structure (II). The reaction of a compound of structure (V) with a compound of structure (II) is however an inefficient reaction providing the compounds of (I) in relatively poor yields (of around 50–60%), with the formation of much iodide waste. Inefficient reactions forming significant unwanted, and difficult to dispose of, side products are undesirable for the preparation of high purity pharmaceutical products on a large scale. The presently claimed reaction, in contrast provides the compounds of structure (I) (prior to any deprotection or salt formation) in yields of >85%, with the products precipitating direct from solution, and isolated by simple filtration. The quality of the product is such that no further recrystallisation step is necessary. The present invention therefore provides a process for the manufacture of compounds of structure (I) in high yield without the need for further purification and in addition avoids the formation of toxic and undesirable iodide waste.

In a further aspect, the present invention also provides a process for the preparation of the intermediate compound of structure (IIIA).

Known processes for the preparation of for example the phthalimide derivative (IIIA) as reported in Chem. Ind. 1957, 1215, J. Med. Chem; 1974, 17, 447–451) and Naturforsch B., 1987, 42, 238–242 report low yields (40–60%) and the formation of unwanted phthalimide by products which have to be removed before further processing. It has now been found that by careful selection of reagents and control of reaction conditions the required compound of structure (IIIA) can be prepared in high yields (80–90%), without the need for further purification.

In a further aspect, the present invention therefore provides, a process for the preparation of a compound of structure (IIIA).

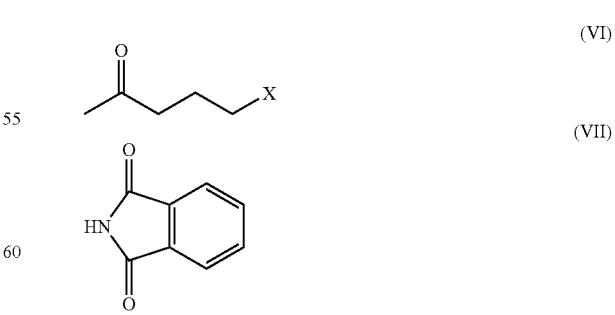
(IIIA)

which comprises reaction of a halo-pentanone of structure (VI)

(VI)

(VII)

in which X is halo, with a compound of structure (VII), in the presence of a base, in a dipolar aprotic solvent, characterised in that the base and compound (VI) are in excess relative to the compound (VII), and that the base is selected from potassium or cesium carbonate.

Suitably, X is halo, preferably iodo.

Suitably the base is cesium carbonate, preferably potassium carbonate.

Suitably the base is in an excess of 1 to 1.5 equivalents relate to the phthalimide (VII), preferably an excess of 1.5 equivalents.

Suitably, the halo pentanone of structure (VI) is in an excess of from 1 to 2 equivalents relative to the phthalimide (VII), preferably an excess of 2 equivalents.

Suitably, the reaction is conducted at elevated temperature, preferably from 60–100° C., most preferably at around 80° C.

Compounds of structure (II) can be prepared by procedures known in the art, in particular for example as descibed in WO 97/13753.

The following examples serve to illustrate the invention, but should not be regarded as limiting the scope thereof:

EXAMPLE 1

Preparation of 8-[(4-amino-1-methylbutyl)amino]-2, 6-dimethoxy-4-methyl-5-(3-trifluoromethylphenoxy) quinoline succinate(tafenoquine) via N-(4-oxopentyl phthalimide

EXAMPLE 1.1

Preparation of N-(4-oxopentyl)pththalimide

A mixture of phthalimide (73.5 g, 0.5 mol), 5-chloro-2-pentanone (120.6 g, 1 mol), potassium carbonate (105 g, 0.75 mol) and N,N-dimethylformamide (500 mL) was stirred and heated to 80° C. for 18–24 h. After cooling to ambient temperature, the mixture was added to ice-cold water (2.5 L). The resulting suspension was stirred at 0–5° C. for 1 hour, then the precipitated product was filtered off, washed thoroughly with water (1.5 L) and dried under high vacuum at 50° C. for 18 hours.

Yield 102 g (88%)

1H NMR (400 MHz): Consistent with structure

HPLC: 98.9% PAR

EXAMPLE 1.2

Preparation of 8-[(4-Phthalimido-1-methylbutyl) amino]-2,6-dimethoxy-4-methyl-5-(3-trifluoromethylphenoxy)quinoline Borane-pyridine complex (Borane concentration ca. 9M; 18 ml, 162 mmol) was added dropwise over ca. 10 minutes to a stirred solution of 8-amino-2,6-dimethoxy-5-(3-trifluoromethyl)phenoxy-4-methylquinoline (108.9 g, 288 mmol) and the product from Example 1.1 (100.0 g, 432 mmol) in glacial acetic acid (855 ml), and the mixture was stirred at ambient temperature for 18 hours.

Methanol (1.5 L) was added, and the mixture stirred at ambient temperature for 2 hours.

The precipitated product was filtered off, washed with methanol (1.1 L) and dried in vacuo at 50° C. for 24 h.

Yield 160.3 g (94%)

Purity according to HPLC PAR=99.5%

1H NMR (400 MHz): Consistent with structure.

EXAMPLE 1.3

Preparation of 8-[(4-amino-1-methylbutyl)amino]-2, 6-dimethoxymethyl-5-(3-trifluoromethylphenoxy) quinoline succinate(tafenoquine)

A stirred mixture of the product from Example 1.2 (159.0 g, 0.27 mol) and hydrazine hydrate (26.2 mL, 0.51 mol, ) in ethanol (1.35 L) was heated under reflux for 7 hours. The mixture was cooled to 80° C. and 1.7M aqueous potassium hydroxide solution (0.8 L) was added. The mixture was cooled to 39° C. and tert-butyl methyl ether (1.35 L) was added. The mixture was cooled to 26° C. and the two phases were separated. The organic phase was washed with 1.7M aqueous potassium hydroxide solution (0.8 L) and brine (475 mL) and evaporated under reduced pressure. The residue was dissolved in IMS (475 mL), succinic acid (41.3 g, 0.35 mol) was added and the stirred mixture was heated under reflux for 30 minutes. The hot solution was filtered through Celite under vacuum and the filter was washed with hot IMS (160 ml). The filtrate and washings were combined, allowed to cool to 35° C. and seeded with tafenoquine crystals (0.1 g). The mixture was cooled to 5° C. over 30 minutes and stirred at 0–5° C. for 1.5 hours. The product was isolated by filtration, washed with cold IMS (2×160 ml) and dried at 45–50° C. under reduced pressure for 2 days to give final product (115.0 g, 74%, purity 98.56%).

EXAMPLE 2

Preparation of 8-[(4-amino-1-methylbutyl)amino]-2, 6-dimethoxy-4-methyl-5-(3-trifluoromethylphenoxy) quinoline succinate(tafenoquine), via 5-nitro-2-pentanone

EXAMPLE 2.1

Preparation of 5-Nitro-2-pentanone

Methyl vinyl ketone (4.17 ml, 0.05 moles), nitromethane (24.4 ml, 0.45 moles) and THF (250 ml) were mixed and stirred together under nitrogen. Potassium fluoride on alumina (10 g) was added and the mixture stirred for 2 hours at ambient temperature. The reaction was filtered and the filtrate was evaporated to give crude 5-nitro-2-pentanone as a pale yellow oil (6.11 g, 93%).

Batches of crude 5-nitro-2-pentanone (total 29.7 g) were combined and purified by vacuum distillation (bp 57–75° C./0.3 mmHg) to give 5-nitro-2-pentanone as a pale yellow oil (17.7 g, 60% recovery).

1H NMR (CDCl$_3$) δ 2.18 (s, 3H, CH$_3$—CO), 2.25 (dt, 2H, CH$_2$), 2.62 (t, 2H, CH$_2$—CO), 4.44 (t, 2H, CH$_2$—NO$_2$).

EXAMPLE 2.2

Preparation of 8-[(1-Methyl-4-nitrobutyl)amino]-2, 6-dimethoxy-4-methyl-5-(3-trifluoromethylphenoxy) quinoline Borane-pyridine complex (borane content ca. 9M; 1.5 ml, 13 mmol) was added to a stirred solution of 8-amino-2,6-dimethoxy-5-(3-trifluoromethyl)phenoxy-4-methylquinoline (8.9 g, 23 mmol) and 5-nitro-2-pentanone (4.6 g, 35 mmol) in glacial acetic acid (70 ml) and the mixture stirred at ambient temperature for 5 hours. The solvent was evaporated, and the brown oily residue dissolved in ethanol (25 ml). The solution was cooled to 4° C. for 18 hours to crystallise the product. The solid product was filtered off, washed with cold ethanol (10 ml) and dried in vacuo at 50° C. for 18 hours to give 8-[(1-methyl-4-nitrobutyl)amino]-2,6-dimethoxy-4-methyl-5-(3-trifluoromethylphenoxy)quinoline as a pale yellow solid (8.2 g, 72%).

m.p. 84.8–85.1° C.

1H NMR (d6-DMSO) δ 1.36 (d, 3H, CH$_3$), 1.78 (m, 2H, CH$_2$), 2.14–2.28 (m, 2H, CH$_2$), 2.55 (s, 3H, CH$_3$—Ar), 3.71 (m, 1H, CH—N), 3.79 (s, 3H, CH$_3$—OAr), 4.01 (s, 3H, CH$_3$—OAr), 4.45 (t, 2H, CH$_2$—NO$_2$), 5.80 (d, 1H, NH), 6.49 (s, 1H, arom H), 6.66 (s, 1H, arom H), 6.94 (d,1H, arom H), 7.07 (s, 1H, arom H), 7.21 (d, 1H, arom H), 7.33 (dd, 1H, arom H).

13C NMR (d6-DMSO) δ 20.9 (CH$_3$), 23.1 (CH$_3$—Ar), 24.2 (CH$_2$), 33.6 (CH$_2$), 48.1 (CH—N), 52.9 (CH$_3$—OAr), 57.0 (CH$_3$—OAr), 75.5 (CH$_2$—NO$_2$), 95.1 (arom CH), 112.0 (arom CH), 115.4 (arom CH), 117.9 (arom CH), 118.2 (arom CH), 119.9 (arom C), 124.0 (q, CF$_3$), 127.3 (arom C), 130.0 (arom CH), 131.0 (arom C), 132.9 (q, arom C—CF3), 141.6 (arom C), 146.4 (arom C), 148.9 (arom C), 159.6 (arom C), 159.7 (arom C).

MS m/z 493 (M$^+$)

Calc: C, 58.41; H, 5.31; N, 8.51. Found: C, 58.15; H, 5.30; N, 8.39.

EXAMPLE 2.3

8-[(4Amino-1-methylbutyl)amino]-2,6-dimethoxy-4-methyl-5-(3-trifluoromethylphenoxy)quinoline succinate A mixture of the product from example 2.2 (7.5 g, 15.2 mmol), ethanol (150 ml) and 5% Pd—C (2 g) was stirred under ca. 1 bar hydrogen for 24 hours at ambient temperature. The catalyst was filtered off and the solvent evaporated to leave a volume of ca. 25 ml. Succinic acid (2.3 g, 19.8 mmol) was added, and the mixture heated under reflux for 30 minutes. The solution was then cooled to 0–5° C., seeded with authentic target compound, and stirred for 2 hours. The crystalline product was filtered off, washed with ethanol (15 ml) and dried in vacuo at 50° C. for 24 hours to give 8-[(4-amino-1-methylbutyl)amino]-2,6-dimethoxy-4-methyl-5-(3-trifluoromethylphenoxy)quinoline succinate as an off-white crystalline solid (6.0 g, 68%).

A portion of the product (4.0 g) was recrystallised from ethanol (15 ml). The crystalline product was filtered off, washed with ethanol (5 ml) and dried in vacuo at 50° C. for 24 hours to give the product as an off-white crystalline solid (3.2 g, 80% recovery).

1H NMR (d6-DMSO) δ 1.07 (d, 3H, CH$_3$), 1.49 (m, 4H, CH$_2$CH$_2$), 2.09 (s,3H, CH$_3$—Ar), 2.27 (s, 4H, succinate), 2.66 (t, 2H, CH$_2$—N), 3.57 (s,3H, CH$_3$—OAr), 3.60 (m, 1H, CH—N), 3.76 (s, 3H, CH$_3$—OAr), 5.66 (d, 1H, NH), 6.49 (s, 1H, arom H), 6.56 (s, 1H, arom H), 6.79 (d, 1H, arom H), 6.84 (s, 1H, arom H), 7.11 (d, 1H, arom H), 7.29 (dd, 1H, arom H).

MS m/z 463 (M$^+$ of free base)

Calc: C, 57.82; H, 5.89; N, 7.23. Found: C, 57.66; H, 5.87; N, 7.14.

What is claimed is:

1. A process for the preparation of a compound of structure (IA) or a pharmaceutically acceptable salt thereof,

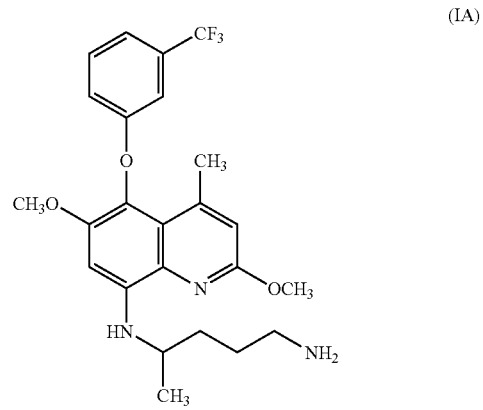

(IA)

which process comprises reaction of a compound of structure (IIA)

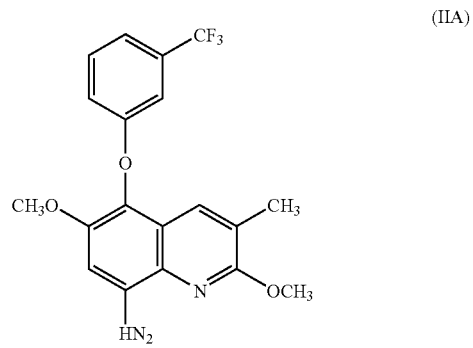

(IIA)

with a compound of structure (IIIA)

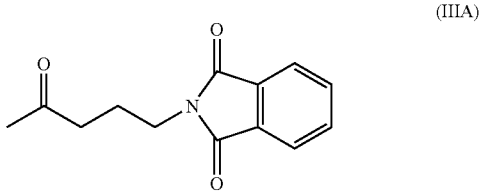

(IIIA)

under reductive alkylation conditions using borane-pyridine complex in acetic acid as solvent, and thereafter, removing the phthalimide protecting group, and optionally thereafter forming a salt.

* * * * *